(12) United States Patent
Zaytseva et al.

(10) Patent No.: US 10,073,049 B2
(45) Date of Patent: Sep. 11, 2018

(54) METHOD FOR DETERMINING THE COMPOSITION AND CRYOLITE RATIO OF SOLID SAMPLES OF POTASSIUM-CONTAINING ELECTROLYTE IN ALUMINUM PRODUCTION BY XRD

(71) Applicant: United Company RUSAL Engineering and Technology Centre, LLC, Krasnoyarsk (RU)

(72) Inventors: Yuliya Nikolaevna Zaytseva, Krasnoyarsk (RU); Sergey Dmitrievich Kirik, Krasnoyarsk (RU); Igor' Stepanovich Yakimov, Krasnoyarsk (RU); Petr Sergeevich Dubinin, Krasnoyarsk (RU); Oksana Evgen'evna Piksina, Krasnoyarsk (RU); Dmitriy Aleksandrovich Simakov, Krasnoyarsk (RU); Aleksandr Olegovich Gusev, Krasnoyarsk (RU); Sergey Grigor'evich Ruzhnikov, Krasnoyarsk (RU)

(73) Assignee: UNITED COMPANY RUSAL ENGINEERING AND TECHNOLOGY CENTRE LLC, Krasnoyarsk (RU)

( * ) Notice: Subject to any disclaimer, the term of this patent is extended or adjusted under 35 U.S.C. 154(b) by 250 days.

(21) Appl. No.: 15/108,096

(22) PCT Filed: Feb. 4, 2015

(86) PCT No.: PCT/RU2015/000061
§ 371 (c)(1),
(2) Date: Jun. 24, 2016

(87) PCT Pub. No.: WO2015/112059
PCT Pub. Date: Jul. 30, 2015

(65) Prior Publication Data
US 2016/0327497 A1 Nov. 10, 2016

(30) Foreign Application Priority Data

Jan. 23, 2014 (RU) ................................ 2014102329

(51) Int. Cl.
*G01N 23/20* (2018.01)
*G01N 23/207* (2018.01)
(Continued)

(52) U.S. Cl.
CPC ............. *G01N 23/207* (2013.01); *C25C 3/06* (2013.01); *C25C 3/20* (2013.01); *G01N 27/26* (2013.01); *G01N 2223/637* (2013.01)

(58) Field of Classification Search
CPC ........ G01N 23/207; G01N 27/26; C25C 3/06; C25C 3/20
See application file for complete search history.

(56) References Cited

FOREIGN PATENT DOCUMENTS

CN 1100807 A 3/1995
CN 102507679 A 6/2012
(Continued)

OTHER PUBLICATIONS

English Machine Translation of Yan et al., CN 102507679 A, Jun. 2, 2012, Translated Online Apr. 2018.*
English Machine Translation of Nikolaevna et al., RU 2418104 C1, May 10, 2011, Translated Online Apr. 2018.*
International Search Report for PCT/RU2015/000061 dated Jun. 25, 2015.

*Primary Examiner* — Lisa Caputo
*Assistant Examiner* — David Z Huang
(74) *Attorney, Agent, or Firm* — Hogan Lovells US LLP

(57) ABSTRACT

This invention relates to producing aluminum by electrolysis of a melt and can be used in the process control of an electrolyte composition by quantitative X-ray phase analysis (XRD) of potassium-containing electrolyte with calcium or calcium and magnesium additives. A quantitative XRD method is employed for analyzing doped samples of crystallized bath samples taken from baths. A weighted ground (Continued)

bath sample is mixed with a weighted quantity of sodium fluoride at a ratio, for example, 1:2 by weight. The weighted quantities are mixed and placed in a furnace (650-750° C. for 20-40 minutes) to dissolve sodium fluoride in the sample and recrystallize the sample with the desired phase composition. The doped sample is placed in a furnace (420-450° C) and held for 15-30 minutes. The doped sample is removed from the furnace and allowed to air cool. The phase composition of the doped sample is analyzed by any quantitative X-ray phase method.

3 Claims, 1 Drawing Sheet

(51) Int. Cl.
    *C25C 3/20*     (2006.01)
    *G01N 27/26*     (2006.01)
    *C25C 3/06*     (2006.01)

(56) References Cited

FOREIGN PATENT DOCUMENTS

| | | |
|---|---|---|
| RU | 2358041 C2 | 6/2009 |
| SU | 548809 A1 | 3/1977 |

\* cited by examiner

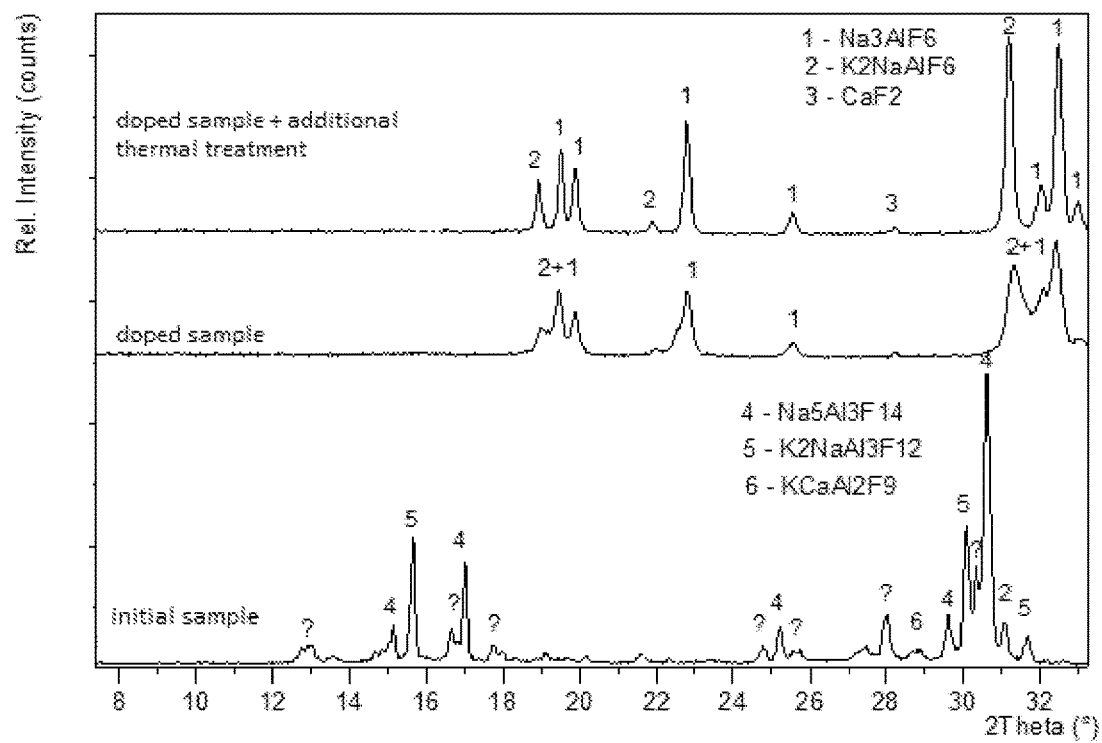

METHOD FOR DETERMINING THE COMPOSITION AND CRYOLITE RATIO OF SOLID SAMPLES OF POTASSIUM-CONTAINING ELECTROLYTE IN ALUMINUM PRODUCTION BY XRD

RELATED APPLICATIONS

This application is a 371 Application of PCT/RU2015/000061 filed on Feb. 4, 2015, which claims the benefit of Russian Application No. RU2014102329 filed on Jan. 23, 2014. The entire disclosures of the prior applications are hereby incorporated by reference herein in their entirety.

This invention relates to the production of aluminum by electrolysis and may be used in determining the composition of potassium-containing electrolyte to regulate process parameters.

Control of electrolyte composition is an important process procedure in electrolytic production of aluminum. During electrolysis bath, the composition and properties of the electrolyte change. In connection with this, the electrolyte is analyzed about once every three days, whereby the electrolyte composition of each bath is corrected. Controlled characteristics of the composition include: cryolite ratio (CR)—the ratio of the total content of sodium fluoride to aluminum fluoride ($[NaF]/[AlF_3]$), content of KF and, in some cases, $CaF_2$, $MgF_2$. The cryolite ratio is responsible for such important parameters of an electrolyte as temperature of crystallization, alumina solubility, electrical conductivity, viscosity and others. The composition is determined by a method of quantitative X-ray phase analysis (XRD) of crystallized electrolyte samples selected from baths. The required accuracy for the determination of CR equals $\Delta = \pm 0.04$ CR units.

The phase composition of solid samples of potassium-containing electrolytes mainly includes the following phases: $Na_5Al_3F_{14}$, $K_2NaAl_3F_{12}$, $K_2NaAlF_6$. However, as XRD shows, additional phases of unknown composition may be present in the samples. Ignoring the latter during analysis distorts the result of determining the CR.

To eliminate the distortion of analysis results, a method for doping a composition of analyzed samples can be used. The method is as follows. A known amount of another agent is added to the samples to be analyzed followed by thermal treatment with the purpose of changing the phase composition of the samples and obtaining samples with known crystalline phases.

A prior art method for preparing samples of calcium-containing electrolytes for subsequent composition analysis by XRD (RF Patent No. 2418104, Int. Cl. C25C3/06, 3/20, publ. May 10, 2011) is as follows. The selected electrolyte samples undergo thermal treatment in a furnace at temperatures of 480-520° C. for 20-40 minutes to improve the diffraction properties of the crystallized phases before the quantitative XRD is carried out.

This method is not directed at the analysis of potassium-containing electrolyte because the applied thermal treatment does not improve the measurement conditions in the quantitative XRD method.

A prior art method for determining the cryolite ratio of electrolyte in aluminum electrolyzers (USSR Inventor's Certificate No. 548809, Int. Cl. G01N 31/16, C01F 7/54, publ. Feb. 28, 1977) is as follows. The starting electrolyte containing magnesium and lithium fluoride additives is sintered with sodium fluoride at temperatures of 600-650° C. The resulting sinter is leached, and the obtained solution is titrated with a 0.05 N thorium nitrate solution to determine the amount of unreacted NaF. Then, the CR of the starting sample is calculated.

This method is not applicable for the analysis of potassium fluoride-containing electrolytes and does not allow determining the composition of the electrolyte sample.

A prior art method for determining the cryolite ratio of electrolyte (RF Patent No. 2424379, Int. Cl. C25C 3/06, publ. Jul. 20, 2011) is as follows. The electrolyte samples containing magnesium and calcium fluoride additives are analyzed by an X-ray fluorescence method and by measuring the intensity of fluorescence in respect of the CR, lines of Na, F, Ca, Mg, the concentrations of elements Na, F, Ca, Mg are determined and the cryolite ratio is determined by the concentrations of Na, F, Ca, Mg. To construct calibration curves for Na, F, Ca, Mg, industry standard electrolyte samples of electrolytic cells in the production of aluminum are used. This method is not applicable for the analysis of electrolytes containing potassium fluoride and does not allow determining the concentration of K.

Publications are known which are devoted to the determination of the cryolite ratio in electrolytes using an X-ray diffraction method (S. D Kirik, N. N. Kulikova, I. S. Yakimov, T. I. Klyueva, I. A. Baranov, V. Yu. Buzunov, V. G. Goloshchapov. Non-Ferrous Metals, 1996, No. 9, pp. 75-77; S. N. Arkhipov, A. A. Stekolshchikov, G. A. Lyutinskaya, L. N. Maximova, L. A. Pyankova. Plant Laboratory. Material Diagnostics 2006, vol. 72, No. 9, pp. 34-36). This method is as follows. Crystalline phases of the components in the cooled electrolyte sample are determined followed by the recalculation into CR values and the content of CaF2 and MgF2 in accordance with the stoichiometry. The quantitative diffraction analysis of fluoride content is based on the external standard method which involves the calculation of the phase concentrations by pre-constructed calibration curves. Total content of calcium fluoride is determined by a fluorescence channel. This method is not applicable to potassium-containing electrolytes as the potassium-containing electrolyte samples comprise phases of unknown composition.

A prior art method for analyzing potassium-containing electrolytes [«Method for determining molecular ratio of acidic KF—NaF—AlF3 electrolyte system» Yan, Hengwei; Yang, Jianhong; Li, Wangxing; Chen, Shazi; Bao, Shengchong; Liu, Dan From Faming Zhuanli Shenqing (2012), CN 102 507 679 A 20,120,620] is as follows. A weighted quantity of NaF at a ratio of 1:2 to the weight of the initial sample is added to a solid electrolyte sample followed by sintering of the sample at a temperature of 600-700° C. for 15-50 min. Then, the resulting sinter is leached, and the amount of unreacted NaF is determined by measuring the solution's conductivity. Then, the CR of the starting sample is calculated. This method does not allow determining the composition of the electrolyte sample. This method of analyzing a potassium-containing electrolyte is taken as a prototype.

BRIEF DESCRIPTION OF THE DRAWINGS

FIG. 1 provides fragments of X-ray patterns for a solid sample of potassium-containing electrolyte: initial, doped and doped with additional thermal treatment. The lower panel shows the X-ray pattern of potassium-containing electrolyte (initial); the middle X-ray pattern is for doped potassium-containing electrolyte, thermal treatment at 750° C. (broad analytical lines); and the upper X-ray pattern shows the sample after thermal treatment at 450° C. (narrow analytical lines with greater intensity).

The object of the proposed method is to increase the accuracy when determining the CR to the ±0.04 abs. CR units.

The technical result which the proposed invention aims to achieve is a controlled change of the phase composition of a sample based on doping the sample and the subsequent thermal treatment to obtain the sample with known crystalline phases, which is necessary for determining the composition of the electrolyte with desired accuracy.

The indicated technical result is achieved by a method for determining the composition and the cryolite ratio of potassium-containing electrolyte comprising obtaining an electrolyte sample from a bath, grinding the sample, adding sodium fluoride to the ground sample, sintering the sample and determining the cryolite ratio and fluoride concentration in the sample wherein according to the claimed method, after sintering, the sample is subjected to an additional thermal treatment until the equilibrium phase composition of $Na_3AlF_6$, $K_2NaAlF_6$, $CaF_2$, NaF is achieved, and the cryolite ratio and the concentration of fluorides in the sample is determined by quantitative X-ray diffraction analysis.

Additional points clarify the method.

Sodium fluoride is added at a ratio of 1:2 to the weight of the sample, and the sintering of the sample is carried out at 650-750° C. for 20-40 minutes.

The sample is subjected to an additional thermal treatment at 420-450° C. for 15-30 minutes.

The claimed method is different from the prior art prototype in that the known quantity of sodium fluoride is added to crystallized samples taken from baths. Samples were sintered at temperatures of 650-750° C. for 20-40 minutes and at 420-450° C. for 15-30 minutes.

The following phases are observed in solid samples of potassium-containing electrolytes $K_2NaAl_3F_{12}$, $Na_5Al_3F_{14}$, $K_2NaAlF_6$, $KCaAl_2F_9$. Phases of unknown composition are also present. Sodium fluoride (NaF) of reagent grade was used as a doping agent. During sintering of the sample with sodium fluoride the following chemical reactions occur:

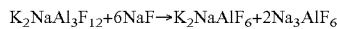

$K_2NaAl_3F_{12}+6NaF \rightarrow K_2NaAlF_6+2Na_3AlF_6$

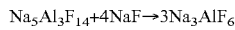

$Na_5Al_3F_{14}+4NaF \rightarrow 3Na_3AlF_6$

$2KCaAl_2F_9+10NaF \rightarrow 2CaF_2+K_2NaAlF_6+3Na_3AlF_6$ and also in the presence of magnesium fluoride:

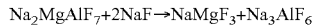

$Na_2MgAlF_7+2NaF \rightarrow NaMgF_3+Na_3AlF_6$

The final phase composition of the sample doped with sodium fluoride is represented by two major phases: $Na_3AlF_6$, $K_2NaAlF_6$, and excess NaF. Calcium ions are present in the $CaF_2$ phase in samples containing calcium. Magnesium ions are present in the $NaMgF_3$ phase in samples containing magnesium.

The formed phases are crystalline.

It was found experimentally that for areas with compositions lying in the region of the CR≥0.8, it is sufficient to introduce a sodium fluoride additive equal to half the weight of the initial sample. The introduction of less sodium fluoride does not provide the desired phase composition with the value of CR≈3.

The need for additional thermal treatment was due to the fact that the X-rays of doped samples weighing up to 3 g sintered at temperatures of 650-750° C. have broad analytical lines, unsuitable for quantitative XRD. Additional thermal treatment of doped samples at a temperature of 420-450° C. provides an X-ray pattern with narrow permitted analytical lines.

The figure presents fragments of X-ray patterns for a solid sample of potassium-containing electrolyte: initial, doped and doped with additional thermal treatment, where: lower X-ray pattern—potassium-containing electrolyte (initial); middle X-ray pattern—doped potassium-containing electrolyte, thermal treatment at 750° C. (broad analytical lines); upper X-ray pattern—subsequent thermal treatment at 450° C. (narrow analytical lines with greater intensity).

The initial sample is multiphase. In addition to basic compounds $Na_5Al_3F_{14}$, $K_2NaAl_3F_{12}$, $K_2NaAlF_6$, it comprises phases, the composition of which is unknown (lines of unknown phases are marked by question marks on the X-ray pattern). During the controlled doping and additional thermal treatment of the sample, the phase composition thereof changes. After this operation, the samples only consist of the known crystalline phases ($Na_3AlF_6$, $K_2NaAlF_6$, $CaF_2$, NaF). Additional thermal treatment leads to an improvement in the radiographic characteristics of the phases: the lines become narrow, and their intensity increases.

Studies revealed that the optimal conditions during the sintering of the electrolyte sample with sodium fluoride are temperatures between 650° C. and 750° C. with calcination times of 20-40 minutes.

An increase of the thermal treatment temperature over 750° C. can lead to the escape of compounds $NaAlF_4$, $AlF_3$, $KAlF_4$ and a change in the sample composition. A thermal treatment temperature of less than 650° C. requires more time for reactions to fully proceed between the phases in the sample and sodium fluoride.

It was experimentally found that 20 minutes was insufficient for all reactions to fully proceed between the phases present in the sample and sodium fluoride. Increasing the duration of thermal treatment by more than 40 minutes is not appropriate because this time is sufficient for all reactions to proceed between the phases present in the sample and sodium fluoride at any degree of mixing.

The subsequent thermal treatment of the doped sample at a temperature of 420-450° C. leads to an improvement in the radiographic characteristics (a reduction in half-width and an increase in the intensity of the analytical lines). A thermal treatment temperature of less than 420° C. is not appropriate because it was established experimentally that the improvement of crystallinity is significantly slower. A thermal treatment temperature over 450° C. does not lead to a significant improvement in X-ray patterns.

It was established experimentally that thermal treatment durations of less than 15 minutes is not sufficient to improve the crystallinity of the doped sample. Thermal treatments of more than 30 minutes are not appropriate because of the increased duration of the analysis.

Therefore, doping should be carried out under the following conditions: a weighted ground sample is mixed with a weighted quantity of sodium fluoride at a ratio of 1:2 by sample weight. The mixture is placed in a closed crucible in a furnace, heated to a temperature of 650-750° C. and held there for 20-40 minutes. Then the doped sample is placed in a furnace, heated to a temperature of 420-450° C. and held there for 15-30 minutes. Then, the sample is removed, and air cooled. Analysis of the phase composition is carried out by any method of quantitative XRD taking into account the quantity of the introduced sodium fluoride. The use of doping followed by the thermal treatment of the doped sample provides samples of equilibrium phase composition and good phase crystallinity, which is a necessary condition for the application of quantitative XRD methods.

These conclusions were made for samples of electrolytes synthesized under laboratory conditions and samples of electrolytes taken from test electrolytic cells. Weight loss during thermal treatment of samples under these conditions did not exceed 1 wt. %.

Calculation of the CR and KF and $CaF_2$ concentrations of initial samples of potassium- and calcium-containing electrolytes can be performed based on the data of quantitative XRD of doped samples according to the following method:

1. Phase concentrations of the doped sample are determined $C_d(Na_3AlF_6)$, $C_d(K_2NaAlF_6)$, $C_d(CaF_2)$, $C_d(NaF)$ by the XRD method, for example, by using calibration curves.

2. Concentrations (wt. %) of fluorides in the doped sample are calculated $C_d(NaF)$, $C_d(KF)$, $C_d(AlF_3)$ $C_d(CaF_2)$:

$$\left.\begin{array}{l} C_d(NaF) = \dfrac{C_d(K_2NaAlF_6)}{Mr(K_2NaAlF_6)} \times Mr(NaF) + \\[6pt] \dfrac{C_d(Na_3AlF_6)}{Mr(Na_3AlF_6)} \times 3Mr(NaF) + C_d(NaF), \\[6pt] C_d(NaF) = 0.17 * C_d(K_2NaAlF_6) + 0.6 * C_d(Na_3AlF_6) + C_d(NaF) \\[6pt] C_d(KF) = \dfrac{C_d(K_2NaAlF_6)}{Mr(K_2NaAlF_6)} \times 2Mr(KF) \\[6pt] C_d(KF) = 0.48 * C_d(K_2NaAlF_6) \\[6pt] C_d(AlF_3) = \dfrac{C_d(K_2NaAlF_6)}{Mr(K_2NaAlF_6)} \times Mr(AlF_3) + \dfrac{C_d(Na_3AlF_6)}{Mr(Na_3AlF_6)} \times Mr(AlF_3), \\[6pt] C_d(AlF_3) = 0.35 * C_d(K_2NaAlF_6) + 0.4 * C_d(Na_3AlF_6) \end{array}\right\} \quad 1$$

3. Weights of fluorides $m_d(NaF)$, $m_d(KF)$, $m_d(AlF_3)$, $m_d(CaF_2)$ in the doped sample:

$$\left.\begin{array}{l} m_d(NaF) = \dfrac{m(\text{sample}) + m(\text{add. NaF})}{100} * C_d(NaF) \\[6pt] m_d(KF) = \dfrac{m(\text{sample}) + m(\text{add. NaF})}{100} * C_d(KF), \\[6pt] m_d(AlF_3) = \dfrac{m(\text{sample}) + m(\text{add. NaF})}{100} * C_d(AlF_3), \\[6pt] m_d(CaF_2) = \dfrac{m(\text{sample}) + m(\text{add. NaF})}{100} * C_d(CaF_2) \end{array}\right\} \quad 2$$

$m$(sample) – weight of the sample $m$(add.NaF) – weight of the added sodium fluoride to the sample 4. The cryolite ratio (CR) and fluoride concentrations in the initial sample:

$$\left.\begin{array}{l} C_{ini}(NaF) = \dfrac{(m_d(NaF) - m(об.NaF)) * 100}{(m_d(NaF) - m(об.NaF) + m_d(KF) + m_d(AlF_3) + m_d(CaF_2))} \\[8pt] C_{ini}(KF) = \dfrac{m_d(KF) * 100}{(m_d(NaF) - m(об.NaF) + m_d(KF) + m_d(AlF_3) + m_d(CaF_2))} \\[8pt] C_{ini}(CaF_2) = \dfrac{m_d(CaF_2) * 100}{(m_d(NaF) - m(об.NaF) + m_d(KF) + m_d(AlF_3) + m_d(CaF_2))} \\[8pt] C_{ini}(AlF_3) = \dfrac{m_d(AlF_3) * 100}{(m_d(NaF) - m(об.NaF) + m_d(KF) + m_d(AlF_3) + m_d(CaF_2))} \end{array}\right\} \quad 3$$

$$CR = 2 * \dfrac{C_{ucx}(NaF)}{C_{ucx}(AlF_3)} \quad 4$$

Exemplary embodiments of the method:

Samples of potassium-containing electrolyte with calcium fluoride additives taken from test electrolytic cells to a conical mold were used as test materials.

EXAMPLE 1

Samples of electrolyte taken into a conical mold from a test electrolytic cell were carefully milled and ground with a weighted quantity of NaF of reagent grade.

The weight of sodium fluoride was half the weight of the initial sample. Then, the components were placed in a closed platinum crucible in a furnace at a temperature of 650-750° C. and held there for 20-40 min. The initial and final weight were recorded. The weight loss was less than 1 wt. %. Control of composition of the samples was performed using the XRD method according to non-standard method of "corundum numbers" (diffractometer X'pert Pro (PANalytical, the Netherlands)). X-ray fluorescence analysis method based on the determination of the elemental composition by the corresponding calibrations (automated wavelength X-ray fluorescence spectrometer XRF-1800 from Shimadzu (with Rh-anode) was used as an arbitration method for controlling the composition of the samples.

Table 1 illustrates phase compositions of four samples of potassium-containing electrolyte with calcium fluoride additives and phase compositions of the corresponding doped samples. The initial samples are multiphase (more than 6 phases), in particular, they contain phases of unknown composition. Practically all phases contain sodium fluoride and/or aluminum. To calculate the CR, it is necessary to determine the content of each phase, and know the chemical composition thereof. The doped samples contained only four crystalline phases and the composition of these phases is known.

TABLE 1

| Phase | Initial samples | | | | Doped samples | | | |
|---|---|---|---|---|---|---|---|---|
| | 1 | 2 | 3 | 4 | 1 | 2 | 3 | 4 |
| $Na_5Al_3F_{14}$ | + | + | + | + | | | | |
| $K_2NaAlF_6$ | + | + | + | + | + | + | + | + |
| $K_2NaAl_3F_{12}$ | + | + | + | + | | | | |
| $AlF_3$ | + | | + | + | | | | |
| $KCaAl2F_9$ | + | + | + | + | | | | |
| $KAlF_4$ | | | + | + | | | | |
| $NaCaAlF_6$ | | + | | | | | | |
| Unknown phases | + | + | + | + | | | | |
| $Na_3AlF_6$ | | | | | + | + | + | + |
| $CaF_2$ | | | | | + | + | + | + |
| NaF | | | | | + | + | + | + |

Table 2 shows the values of CR (CR units) for samples of potassium-containing electrolyte with calcium fluoride additives obtained by formula 4 from the composition of the doped samples. The accuracy of determining the CR in the initial samples is assessed below.

TABLE 2

| | CR obtained by formula 4 | |
|---|---|---|
| No. | XRS | XRD |
| 1 | 0.86 | 0.91 |
| 2 | 1.02 | 1.09 |
| 3 | 0.9 | 0.98 |
| 4 | 1.03 | 0.99 |
| 5 | 0.82 | 0.89 |
| 6 | 1.16 | 1.2 |
| 7 | 1.19 | 1.22 |
| 8 | 1.12 | 1.17 |
| 9 | 1.11 | 1.13 |
| 10 | 1.24 | 1.2 |
| 11 | 1.15 | 1.19 |
| 12 | 1.27 | 1.31 |
| 13 | 1.27 | 1.29 |
| 14 | 1.31 | 1.33 |
| 1. | 1.33 | 1.38 |
| Mean values ΔCR (XRS − XRD) | −0.03 | |
| SD ΔCR | 0.03 | |

The CR of samples calculated according to the XRD data for doped samples taking into account the introduced sodium fluoride, is overstated by 0.03 CR units relative to CR values calculated according to XRS with standard deviation of 0.03 CR units.

Table 3 shows the concentrations of calcium and potassium fluoride (wt. %) for potassium-containing electrolyte samples obtained by formula 3 from the composition of doped samples. The accuracy of determining the content of potassium and calcium fluoride in the initial samples is assessed below.

TABLE 3

| | C(KF) | | C(CaF$_2$) | |
|---|---|---|---|---|
| No. | XRS | XRD | XRS | XRD |
| 1 | 17.56 | 15.66 | 1.10 | 1.1 |
| 2 | 16.50 | 16.12 | 1.30 | 1.3 |
| 3 | 18.07 | 15.14 | 3.34 | 3.5 |
| 4 | 16.16 | 13.85 | 3.46 | 3.5 |
| 5 | 17.89 | 17.20 | 2.85 | 2.9 |
| 6 | 9.20 | 6.10 | 3.88 | 3.82 |
| 7 | 16.68 | 13.66 | 4.12 | 4.17 |
| 8 | 8.07 | 5.59 | 4.53 | 3.98 |
| 9 | 7.80 | 6.31 | 4.52 | 4.00 |
| 10 | 11.96 | 11.07 | 5.66 | 5.70 |
| 11 | 12.55 | 9.95 | 5.84 | 6.11 |
| 12 | 9.47 | 6.41 | 4.76 | 4.78 |
| 13 | 8.02 | 5.39 | 5.27 | 5.33 |
| 14 | 7.25 | 6.22 | 5.48 | 5.49 |
| 15 | 8.68 | 6.76 | 5.05 | 5.32 |
| Mean values ΔCR (XRS − XRD) | 2.03 | | 0.01 | |
| SD ΔC | 0.93 | | 0.23 | |

The obtained standard deviations reflect the cumulative margins of error of 2 techniques and XRF and XRD.

The method for doping solid electrolytes samples with sodium fluoride at a temperature of 650-750° C. with subsequent thermal treatment at 420-450° C. may be successfully employed for the analysis of potassium-containing electrolytes.

As is demonstrated by the above examples, doping of electrolyte samples followed by thermal treatment allows achieving good crystallinity of phases and reproducibility of the phase composition of analyzed samples, which is necessary for the application of the quantitative XRD.

The results of experiments on doping with subsequent thermal treatment of industrial electrolytes allow us to recommend this method for the preparation and analysis of samples with the required CR accuracy Δ=±0.04 CR units.

The invention claimed is:

1. A method for determining the composition and the cryolite ratio of potassium-containing electrolyte comprising obtaining an electrolyte sample from a bath, grinding the sample, adding sodium fluoride to the ground sample, sintering the sample and determining the cryolite ratio and fluoride concentration in the sample wherein after sintering, the sample is subjected to an additional thermal treatment until the equilibrium phase composition of $Na_3AlF_6$, $K_2NaAlF_6$, $CaF_2$, NaF is achieved, and the cryolite ratio and the concentration of fluorides in the sample is determined by quantitative X-ray phase analysis.

2. The method of claim 1, wherein sodium fluoride is added at a ratio of 1:2 to the weight of the sample, and the sintering of the sample is carried out at 650-750° C. for 20-40 minutes.

3. The method of claim 1, wherein the sample is subjected to an additional thermal treatment at 420-450° C. for 15-30 minutes.

* * * * *